United States Patent
Schock et al.

(10) Patent No.: US 6,537,254 B1
(45) Date of Patent: Mar. 25, 2003

(54) UNIVERSAL PROTECTIVE CATHETER SLEEVE

(75) Inventors: Robert B. Schock, Sparta, NJ (US); Manuel Marques, Clifton, NJ (US); Frank Frisch, Succasunna, NJ (US); Jeffrey McGinley, Lincoln Park, NJ (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

(21) Appl. No.: 09/347,868

(22) Filed: Jul. 6, 1999

(51) Int. Cl.[7] .................. A61M 5/00; A61M 5/178; A61M 25/16
(52) U.S. Cl. .................. 604/171; 604/167.03; 604/535
(58) Field of Search .................. 604/167.01–167.06, 604/163, 171, 264, 256, 523, 533, 534, 535, 537–539

(56) References Cited

U.S. PATENT DOCUMENTS

| | | | | |
|---|---|---|---|---|
| 3,757,771 A | * | 9/1973 | Ruegg et al. | ............... 600/360 |
| 3,825,001 A | * | 7/1974 | Bennet et al. | |
| 4,235,232 A | * | 11/1980 | Spaven et al. | |
| 4,738,658 A | | 4/1988 | Magro et al. | ............... 604/53 |
| 4,767,409 A | | 8/1988 | Brooks | ............... 604/171 |
| 5,125,904 A | * | 6/1992 | Lee | |
| 5,147,314 A | | 9/1992 | Vaillancourt | ............... 604/158 |
| 5,250,033 A | * | 10/1993 | Evans et al. | ............... 604/160 |
| 5,254,097 A | * | 10/1993 | Schock et al. | |
| 5,364,366 A | * | 11/1994 | Rom et al. | ............... 604/163 |
| 5,478,326 A | | 12/1995 | Shiu | ............... 604/264 |
| 5,685,858 A | | 11/1997 | Kawand | ............... 604/171 |
| 5,715,815 A | * | 2/1998 | Lorenzen et al. | ............ 128/207.14 |
| 5,827,227 A | * | 10/1998 | DeLago | |

* cited by examiner

Primary Examiner—Michael J Hayes
(74) Attorney, Agent, or Firm—Abraham Ronai

(57) ABSTRACT

A protective sleeve for a catheter having a distal end capable of (i) being disposed within and engaging a majority of existing hemostatic valves; and (ii) capable of being partially inserted into a patient, thus, securing the sleeve to the patient in a sheathless catheter insertion procedure.

5 Claims, 3 Drawing Sheets

UNIVERSAL PROTECTIVE CATHETER SLEEVE

BACKGROUND OF THE INVENTION

1. Field of the Invention

The invention relates to a universal catheter guard. More particularly, the invention relates to a protective catheter sleeve capable of engaging a majority of existing hemostatic valves having widely differing hub designs.

2. Description of the Prior Art

Intra-aortic balloon (IAB) catheters are used in patients with left heart failure to increase coronary artery perfusion, decrease the workload of the left ventricle, and allow healing of the injured myocardium. The catheters, approximately 1 meter long, have an inflatable and deflatable balloon at the distal end. The catheter is typically inserted into the femoral artery, through an insertion sheath, and moved up the descending thoracic aorta until the distal tip of the balloon is positioned just below or distal to the left subclavian artery. A passageway for inflating and deflating the balloon extends through the catheter and is connected at its proximal end to an external pump. The proximal end of the catheter remains outside of the patient's body.

The insertion sheath generally has a hemostatic valve at one end. The purpose of the hemostatic valve is to prevent blood from traveling up the annular space between the catheter and the insertion sheath and escaping from the proximal end of the insertion sheath. The hemostatic valve generally has a hub for connection with a collapsible polymeric protective sleeve. Said sleeve is disposed about the catheter, and in its extended state, spans from the proximal end of the insertion sheath to the proximal end of the intra-aortic balloon catheter. The distal end of the sleeve has a collar which when disposed about the hemostatic valve hub secures the distal end of the sleeve to the hemostatic valve. The purpose of the sleeve is to keep the catheter free of contamination so as to prevent infection. The area where the catheter exits the skin of the patient is particularly sensitive to infections or irritation because it is essentially an open wound.

As a result of recent design developments in the IAB catheter field, a long awaited 8 Fr. catheter is now available from Datascope Corp. (Montvale, N.J.). One valuable feature of the 8 Fr. catheter is that due to its reduced size it is capable of passing through an already inserted sheath used for a previous procedure, such as angiography or angioplasty, which generally utilize sheaths that accommodate 8 Fr. catheters. Thus, after an angioplasty procedure, for example, rather than removing the angioplasty insertion sheath and replacing it with an IAB catheter insertion sheath, the IAB catheter can now be inserted into the existing angioplasty insertion sheath.

Given the use of the 8 Fr. IAB catheter with multiple insertion sheaths, the need exists for a protective sleeve having a universal connector capable of connecting to a majority of similarly sized insertion sheaths.

In sheathless procedures, the protective sleeve cannot be connected to the proximal end of the insertion sheath. It is generally left hanging loose, adjacent the insertion site. As a result, the sleeve may move and expose a portion of the catheter, thus increasing the chances of infection. Therefore, the need exists for a protective sleeve capable of being locked in place adjacent the insertion site during sheathless insertion of an IAB catheter.

SUMMARY OF THE INVENTION

Accordingly, it is an object of the invention to produce a protective sleeve for a catheter capable of connecting at its distal end to a majority of existing hemostatic valves.

It is another object of the invention to produce a protective sleeve capable of being safely used in a sheathless IAB catheter insertion procedure.

It is still another object of the invention to produce a protective sleeve capable of being partially inserted into the patient, during a sheathless procedure, thus, preventing exposure of the catheter.

The invention is a protective sleeve for a catheter having a distal end capable of (i) being disposed within and engaging a majority of existing hemostatic valves; and (ii) capable of being partially inserted into a patient, thus, securing the sleeve to the patient in a sheathless catheter insertion procedure.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Note that the proximal and distal directions, as herein used, are relative to the heart of patient. Therefore, the further distal a portion of a catheter is, the closer it is to the heart after insertion of the catheter.

Figure 1:
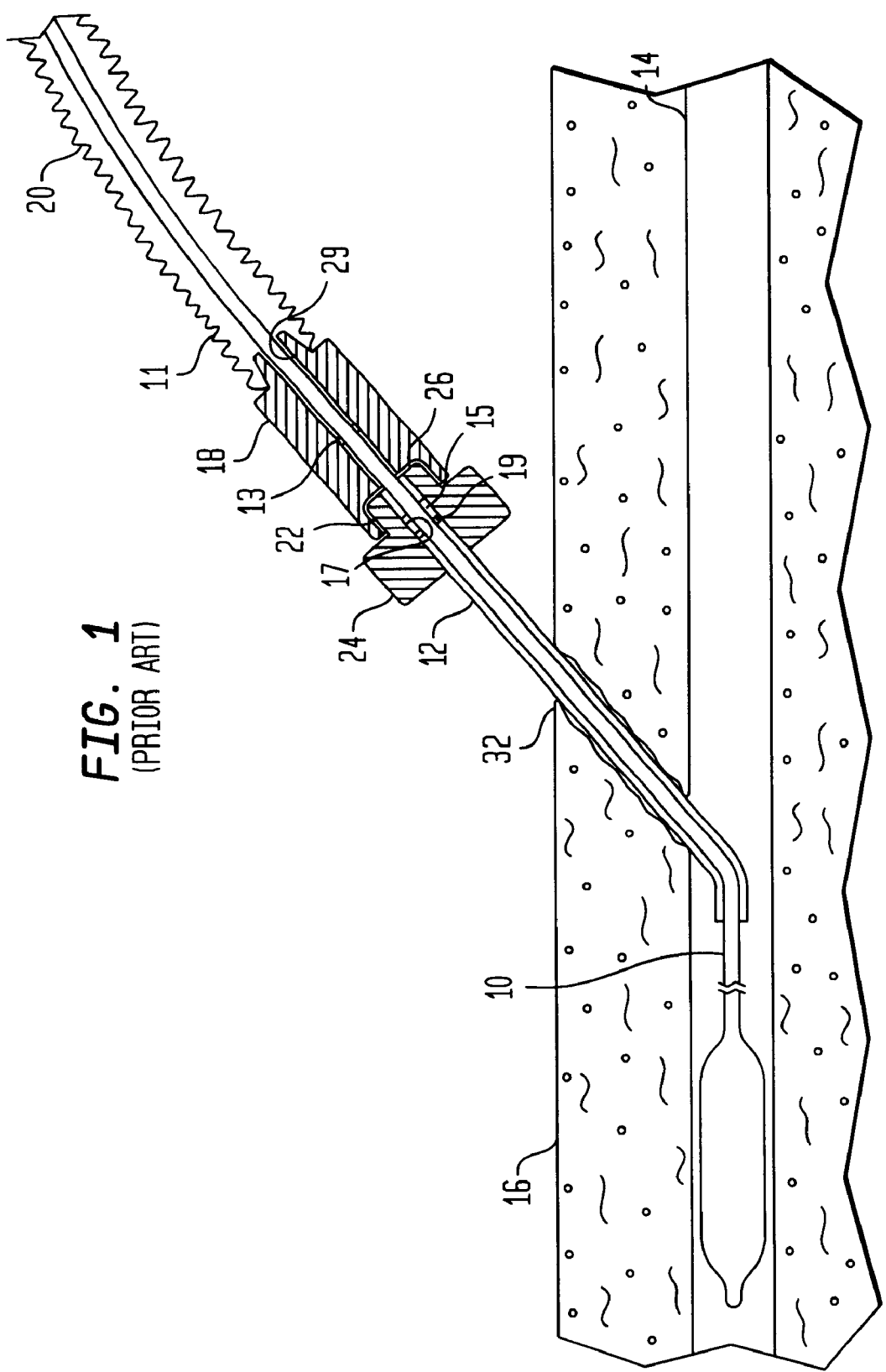
FIG. 1 is a longitudinal cross section of a prior art protective catheter sleeve connected to a hemostatic valve.

FIG. 1 illustrates a longitudinal cross section of a catheter 10 inserted percutaneously through an insertion sheath 12 into a blood vessel 14 of a patient 16. A hemostatic valve 24 has a hub 26 and is connected to or integrally formed with the insertion sheath 12. The sleeve 20 is disposed about the catheter 10 and is made from a collapsible polymeric material. A sheath seal 18, fixedly connected to a distal end 11 of a prior art protective catheter sleeve 20, is removably connected to a proximal end 22 of the hemostatic valve 24. More specifically, the sheath seal 18 is disposed about the hemostatic valve hub 26 and either frictionally engages or snaps onto said hub 26. Alternatively, for insertion sheaths without a hemostatic valve, sheath seal 18 is disposed about a distal end of the insertion sheath 12. An inner surface 17 of the hemostatic valve 24 defines hemostatic valve lumen 15. A diaphragm 19, projecting from the inner surface 17 of the hemostatic valve 24 into the hemostatic valve lumen 15, creates a seal between the hemostatic valve 24 and the catheter 10. A valve 13, projecting from an inner surface 29 of the sheath seal body 30, creates a seal between catheter 10 and sheath seal body 30.

It is clear from FIG. 1 that the prior art protective catheter sleeve 20 is limited in that it can only be connected to hemostatic valves having hubs or ends specifically designed to mate with sheath seal 18.

Figure 2:
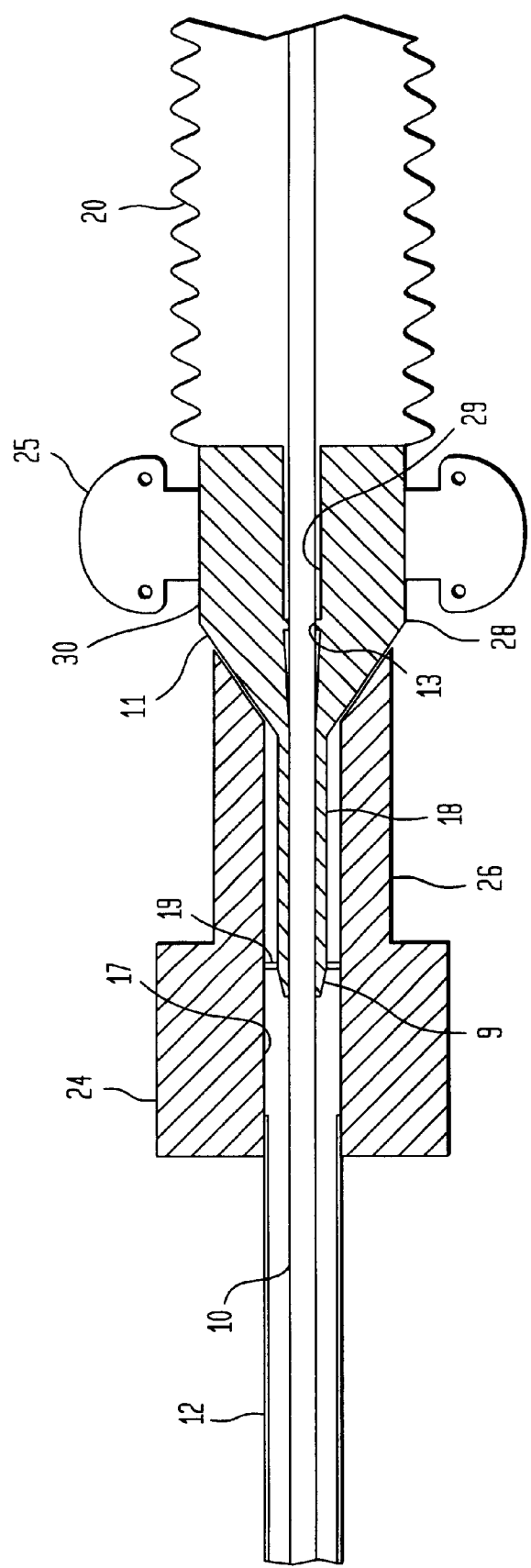
FIG. 2 is a longitudinal cross section of the protective catheter sleeve of the present invention engaging a hemostatic valve.

FIG. 2 illustrates a longitudinal cross sectional view of an improved catheter protective sleeve 20 fixedly attached to a tip portion or sheath seal body 30. The sleeve 20 is shown independent of the patient 16 (FIG. 1) and the catheter 10 (FIG. 1) for clarity. A distal portion 18 of the sheath seal body 30 frictionally engages hemostatic valve diaphragm 19. A distal end 9 of the distal portion 18 is preferably tapered. A middle portion 11 of the sheath seal body 30 has a taper which mates with and fits snugly in an internal taper on a proximal end of inner surface 17. The sheath seal body 30 may have suture pads 25 for securing the sleeve 20 to the patient. The sleeve 20 is preferably made from a collapsible "crunchable" polymeric material which allows the sleeve 20 to be used with catheters of various lengths. Valve 13, projecting from an inner surface 29 of the sheath seal body 30, creates a seal between catheter 10 and sheath seal body 30.

In an alternate embodiment of the invention, an elevation (not shown) projecting from an outer surface 28 of the sheath seal body 30 may frictionally engage inner surface 17 of the hemostatic valve hub 26 to secure the connection between the sleeve 20 and the hemostatic valve 24. Sheath seal body 30 may engage hemostatic valve 24 by any means known in the art to engage two, at least partially, telescoping bodies.

Note that use of the sleeve 20 of the present invention is anticipated with an insertion sheath without a hemostatic valve 24. In such a situation the sheath seal body 30 of the sleeve 20 would engage a proximal portion of the inner surface of the insertion sheath. Note further that a strain relief device (not shown) may be incorporated into the design of the sheath seal body 30.

Figure 3:
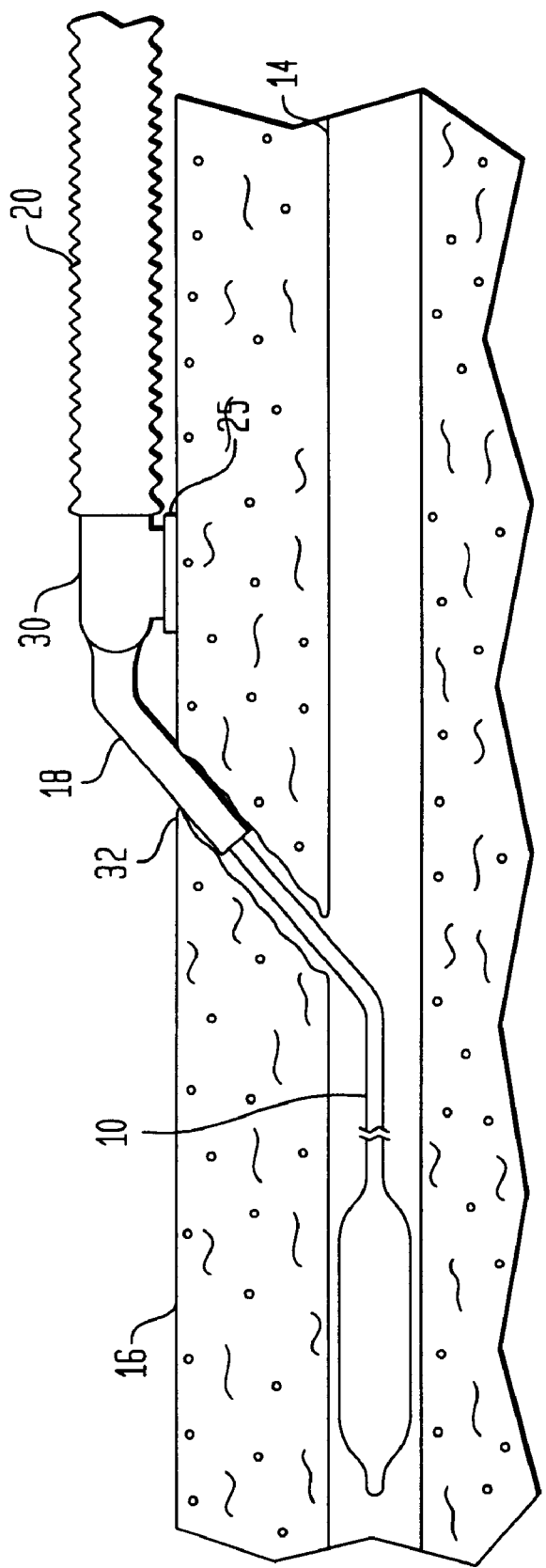
FIG. 3 is a side view of the protective catheter sleeve of the present invention being used in a sheathless procedure.

In sheathless procedures, a portion of the distal portion 18 of the sheath seal body 30 may be inserted directly into the patient 16 at the insertion site 32 of the catheter 10 so as to hold the sheath seal body 30 in place, as illustrated in FIG. 3. Securing the sheath seal body 30 in this manner assures that the catheter remains covered, and thus, reduces the chance of infection. The distal portion 18 of the sheath seal body 30 does not enter the blood vessel 14 of the patient 16.

Note that although the protective sleeve of the present invention is illustrated for use with an intra-aortic balloon catheter, use of the protective sleeve is anticipated with other types of catheters.

What is claimed is:

1. A method for maintaining the cleanliness of a catheter inserted into a patient through an insertion sheath comprising the steps of:

disposing a protective sleeve about an exposed portion of the catheter, said protective sleeve having a collapsible polymeric portion and a body portion connected to a distal end of the collapsible polymeric portion, said body portion comprising a distal tip portion and a proximal end, said insertion sheath comprising a valve hub, said valve hub comprising a hemostatic valve, and advancing at least a portion of the tip portion into the valve hub in between the catheter and the hemostatic valve so as to create an engagement between the tip portion and the hemostatic valve and to create an engagement between an inner surface of the valve hub and a portion of the body portion between the tip portion and proximal end of the body portion.

2. The method as claimed in claim 1 wherein the hemostatic valve comprises a diaphragm projecting from an inner surface of the valve hub.

3. The method as claimed in claim 1 wherein the tip portion is made from a polymeric material.

4. The method as claimed in claim 1 wherein the catheter is an intra-aortic balloon catheter.

5. The method as claimed in claim 1 wherein the portion of the body portion between the tip portion and proximal end of the body portion is engaged to a portion of the inner surface of the valve hub having a taper.

* * * * *